United States Patent

Swisher et al.

[11] Patent Number: 5,865,408
[45] Date of Patent: Feb. 2, 1999

[54] FOOTSTAND FOR CHEST DRAINAGE UNIT

[75] Inventors: David Rork Swisher, St. Charles; Robert Walsh, St. Peters; Eugene E. Weilbacher, Ellisville; Jacky Yam, St. Louis, all of Mo.

[73] Assignee: Tyco Group S.a.r.l., Luxembourg, Luxembourg

[21] Appl. No.: 826,614

[22] Filed: Apr. 4, 1997

[51] Int. Cl.$^6$ ................................................. F16M 11/24
[52] U.S. Cl. ................................. 248/188.12; 604/322
[58] Field of Search ............................. 248/188.2, 188.1, 248/188.3, 131, 139, 144, 398, 415, 404, 188.8; 604/322, 321

[56] References Cited

U.S. PATENT DOCUMENTS

| | | | |
|---|---|---|---|
| 4,449,969 | 5/1984 | Schweizer | 604/322 |
| 4,955,873 | 9/1990 | Rajlevsky | 604/322 |
| 5,401,262 | 3/1995 | Karwoski et al. | 604/321 |
| 5,601,541 | 2/1997 | Swisher | 604/322 |
| 5,967,586 | 12/1997 | Lybarger | 248/188.2 X |

*Primary Examiner*—Ramon O. Ramirez
*Attorney, Agent, or Firm*—David A. Warmbold

[57] ABSTRACT

A footstand for stabilizing a body of a medical device against being overturned. The body may especially be a chest drainage unit (CDU) designed and configured to receive and collect fluids from a medical patient. The invention comprises at least one stand coupled to the body and adapted for deployment to a position for stabilizing the body against upset. The CDU body is a generally upstanding rectangular box having a pair of depending feet, one foot on each side of the body. The stand, is rotatably connected to the bottom of the CDU body and is provided with a height adjustment feature which allows the stand to be rotated between a first undeployed position wherein the stand covers or encloses the depending fee of the CDU body while providing a relatively smooth and continuous bottom stand surface to a second deployed position wherein the bottom stand surface is at the same height or in the same horizontal plane as the bottom of the depending feet of the CDU body to provide a solid and secure footstand for the CDU body. It is desirable to provide a footstand for a CDU which provides a smooth contoured surface for the CDU bottom when the footstand is in its first undeployed position so that the CDU bottom will not puncture the sterile package during transportation of the CDU to an end user or during storage of the CDU prior to use or during disposal of the CDU after use in a hazardous disposal bag.

19 Claims, 8 Drawing Sheets

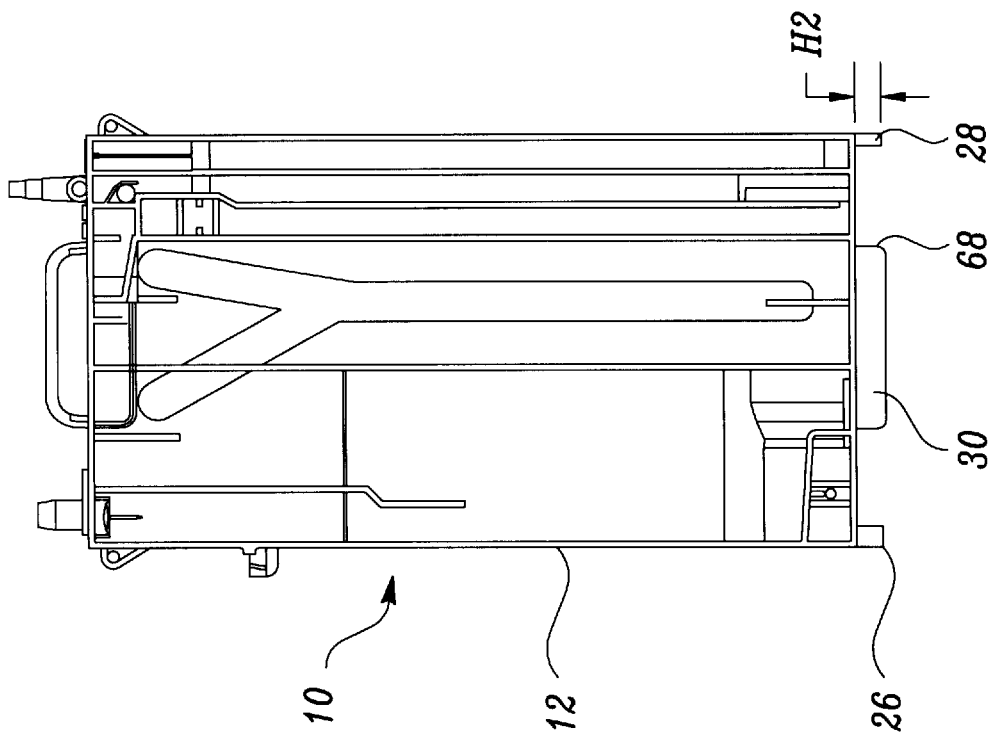
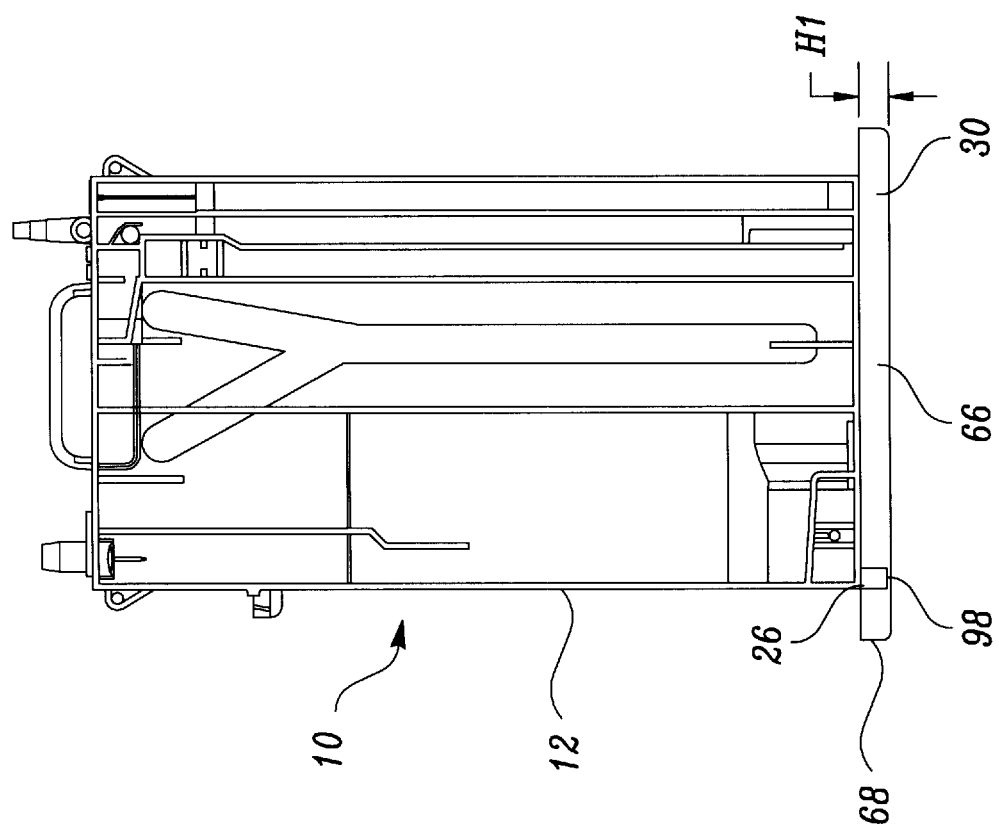

FOOTSTAND FOR CHEST DRAINAGE UNIT

1. Field of the Invention

The present invention relates generally to a footstand or support stand for a free standing medical device. More specifically, the invention relates to a footstand suitable for use with a chest drainage unit (CDU) which footstand can be deployed to stabilize the CDU in a free standing upright position and when rotated to a undeployed or secured position will protect the bottom of the CDU.

2. Prior Art

There have been a number of devices introduced in the marketplace for use as a base or stand in an effort to keep a CDU or other drainage device in an upright position. U.S. Pat. No. 4,955,873 to Rajlevsky shows a CDU having at least one stand rotatably coupled to the bottom of the CDU body and adapted for deployment in a position for stabilizing the CDU body against being upset. The CDU body also has a plurality of depending feet on its outermost sides to help stabilize the CDU body when the CDU stand is rotated ninety (90) degrees to support the CDU from being upset or overturned. When the rotating stand is returned to its unsupporting position, the depending feet and stand are flush with one another. However, the depending feet are unprotected and during transportation of the CDU the feet can be broken off the CDU body. Furthermore, during transportation of the CDU in its sterile package to an end user the depending feet can puncture the sterile package thereby destroying the sterility of the CDU and possibly causing harm to a patient utilizing such CDU.

U.S. Pat. No. 5,401,262 to Karwoski et al. shows a CDU or fluid collection vessel having a generally rectangular body having a rotatable pedestal or stand for supporting the CDU from being upset or overturned. The CDU shown also has a plurality of depending feet or support edges (see FIGS. 3 and 11, reference numerals 139a and 139b of Karwoski et al.) which are also prone to breaking off the CDU body or puncturing the CDU's sterile package during transportation of the CDU to its end user or storage of the CDU prior to its use.

As of yet, nothing in the prior art has addressed the problem of providing a footstand or support stand for a medical device or CDU which when in its deployed position stabilizes the CDU against being upset or overturned and when the footstand is rotated to its undeployed position protects the bottom of the CDU body and any depending stabilizing feet while providing a smooth bottom contour which minimizes any chance of puncturing its sterile package during transportation or storage of the CDU.

SUMMARY OF THE INVENTION

It is an object of the present invention to provide a footstand or support stand for a free standing medical device which supports the medical device in an open position protects the bottom of the medical device in a closed position.

It is another object of the present invention to provide a footstand for a chest drainage unit (CDU) which supports the CDU when in an open position and provides a smooth contoured surface for the CDU bottom when in a closed or unsupported position so that the CDU bottom will not puncture the sterile package during transportation of the CDU to its end user or storage of the CDU prior to its use.

It is another object of the present invention to provide a footstand for a CDU which supports the CDU when in an open position and provides the CDU with a smooth contoured bottom surface when in a closed or unsupported position so that the CDU bottom will not puncture a hazardous waste disposal bag upon disposal of the CDU after use.

These and other objects are realized in a footstand for stabilizing a body of a free standing medical device against being overturned. The body may especially be a chest drainage unit (CDU) designed and configured to receive and collect fluids from a medical patient. However, it is not intended that this invention be limited for use only with a CDU and, obviously, could be used to stabilize and support any free standing medical device. The invention comprises at least one stand coupled to the body and adapted for deployment to a position for stabilizing the body against upset. The CDU body is a generally upstanding rectangular box having a pair of depending feet, one foot on each side of the body. The stand is rotatably connected to a central location on the bottom of the CDU body. The stand is provided with a height adjustment means which allows the stand to rotate between a first undeployed position wherein the stand covers or encloses the depending feet of the CDU body to a second deployed position wherein the bottom surface of the stand is at the same height or in the same horizontal plane as the bottom of the depending feet of the CDU body to provide a solid and secure support for the CDU body.

In a preferred form, the stand includes a footstand retainer wherein the footstand retainer, stand and CDU bottom surface all have matching helical or spiral ramps which interact to change the positions of the stand relative to the CDU body upon rotation of the stand. The footstand retainer can be connected to the CDU bottom sandwiching the stand between the CDU bottom and footstand retainer. The stand is adapted for movement between first and second positions, with the stand at the second position stabilizing the CDU body against upset. When the stand is in its first, undeployed position, the stand covers a pair of depending feet extending from the bottom of the CDU body and protects the bottom of the CDU bottom. The stand is rotatable to a second, deployed position where the stand uncovers the depending feet and moves closer to the CDU body such that the bottom of the stand is even with or in the same plane as the bottom of the depending feet of the CDU body.

The various features of novelty which characterize the invention are pointed out with particularity in the claims annexed to and forming a part of this disclosure. For a better understanding of the invention, its operating advantages and specific results obtained by its use, reference should be made to the corresponding drawings and descriptive matter in which there is illustrated and described various embodiments of the invention.

BRIEF DESCRIPTION OF THE DRAWINGS

FIG. 6 an enlarged front view of the CDU body without front face cover showing the footstand in a first, undeployed position protecting the bottom of the CDU.

FIG. 7 is an enlarged front view of the CDU body without front face cover showing the footstand in a second, deployed position for supporting the CDU against being upset.

DETAILED DESCRIPTION OF THE INVENTION

Figure 1:
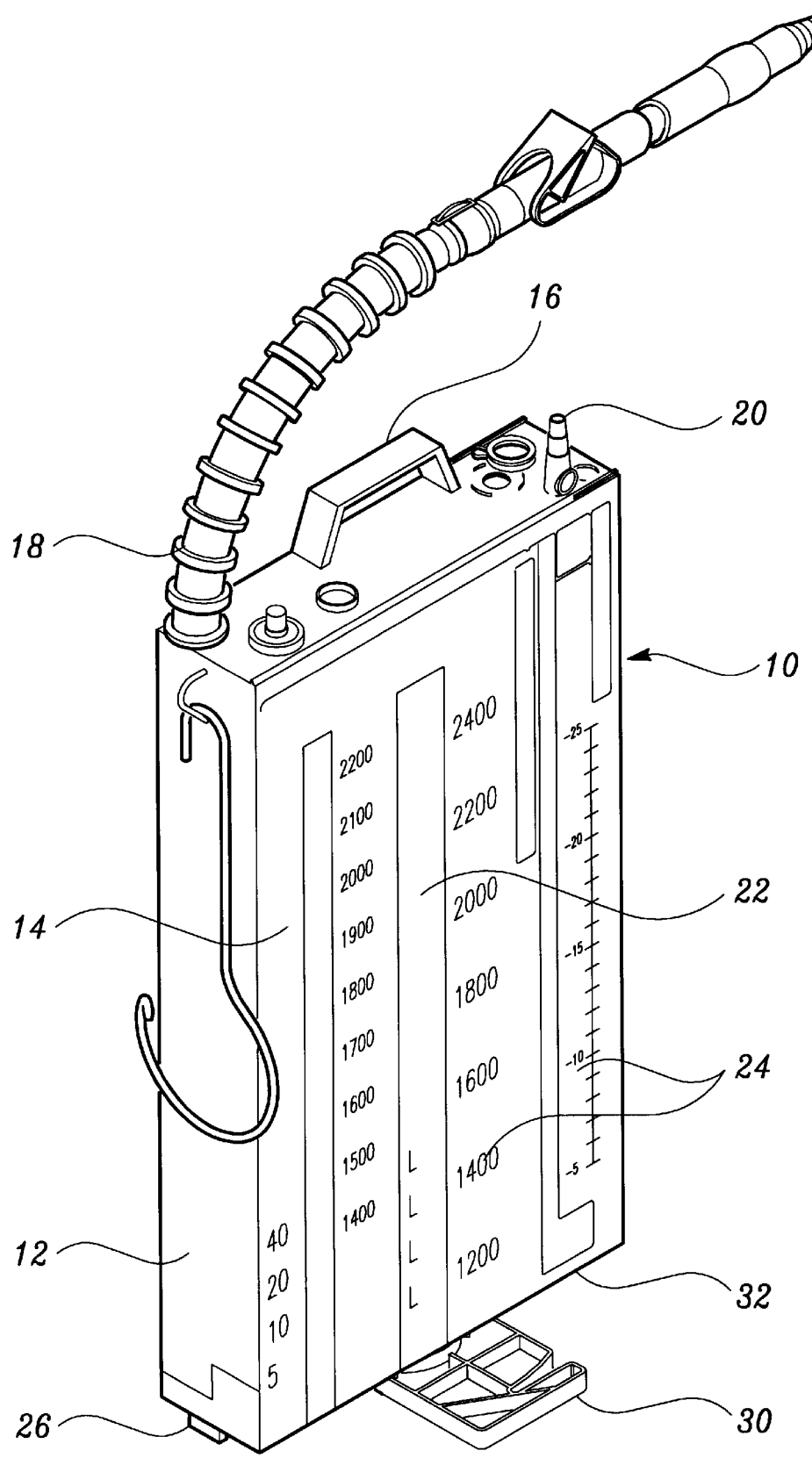
FIG. 1 is a perspective view of the footstand for a CDU in accordance with the principles of the present invention, showing the footstand in a deployed position stabilizing the CDU body against being overturned.

The description presented herein refers to the accompanying drawings in which like reference numerals refer to like parts throughout the several views. First, referring to FIG. 1, there is illustrated a perspective representation of a chest drainage unit (CDU) 10 of the preferred embodiment, with CDU body 12 forming a collection chamber 14 for collecting fluids drained from a patient, handle 16, patient connection tube 18 and suction source connection inlet 20. The CDU body 12 has a face plate 22 which covers and seals the front of the CDU body. The face plate 22 may have numerical and textural indicia 24 which allow a user of the CDU to monitor the various functions and parameters of the CDU during use.

Figure 2:
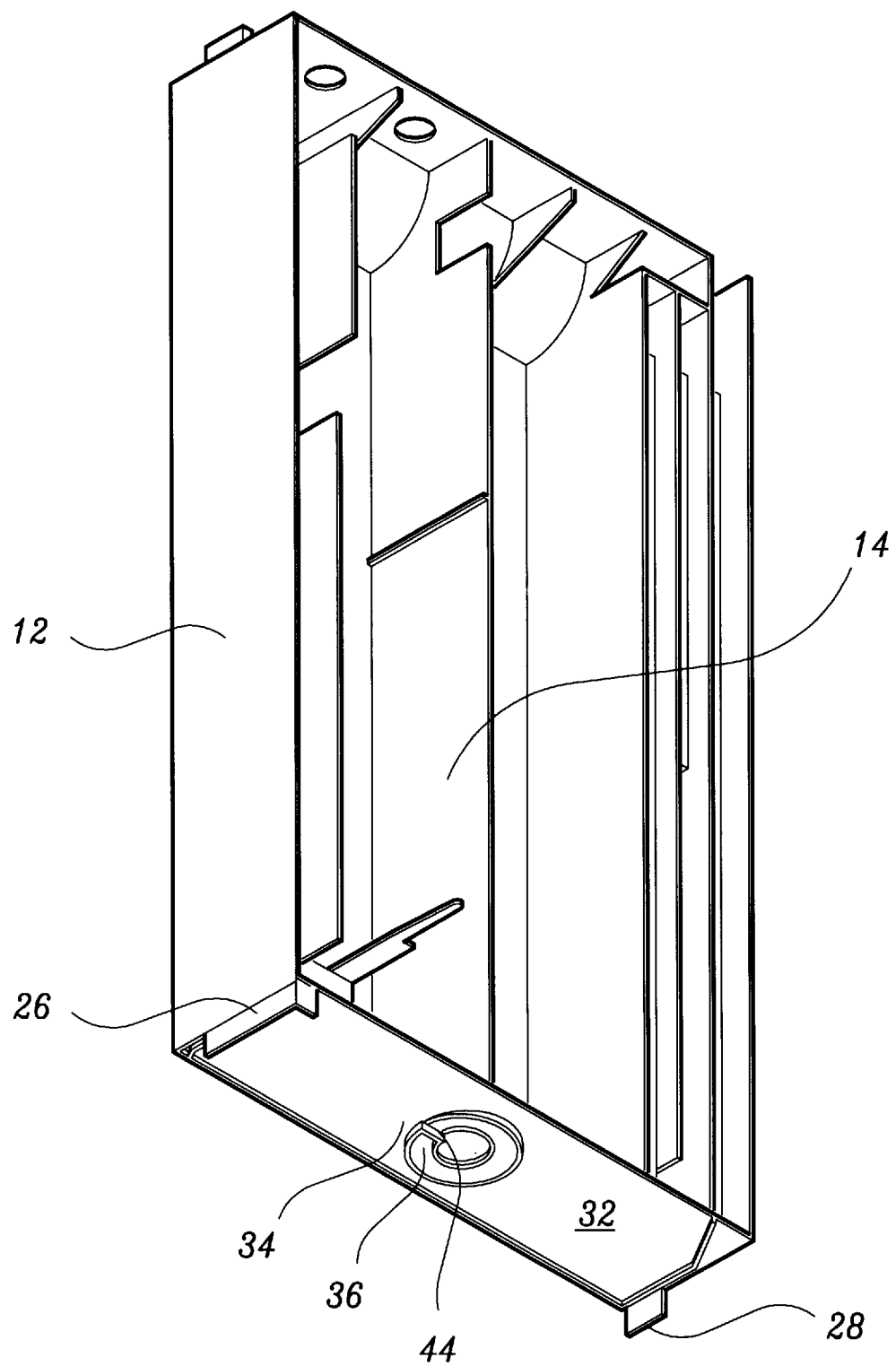
FIG. 2 is a perspective view of the CDU body without front cover showing the bottom of the CDU body.

The CDU of FIGS. 1 and 2 have a pair of depending feet 26 and 28, one foot extending down from each side of the CDU body 12. A footstand or stand 30 is rotatably connected to the bottom 32 of the CDU body 12 as discussed more fully below. The stand 30 is shown in FIG. 1 in a deployed position supporting the CDU from being upset or tipped over.

Figure 5:
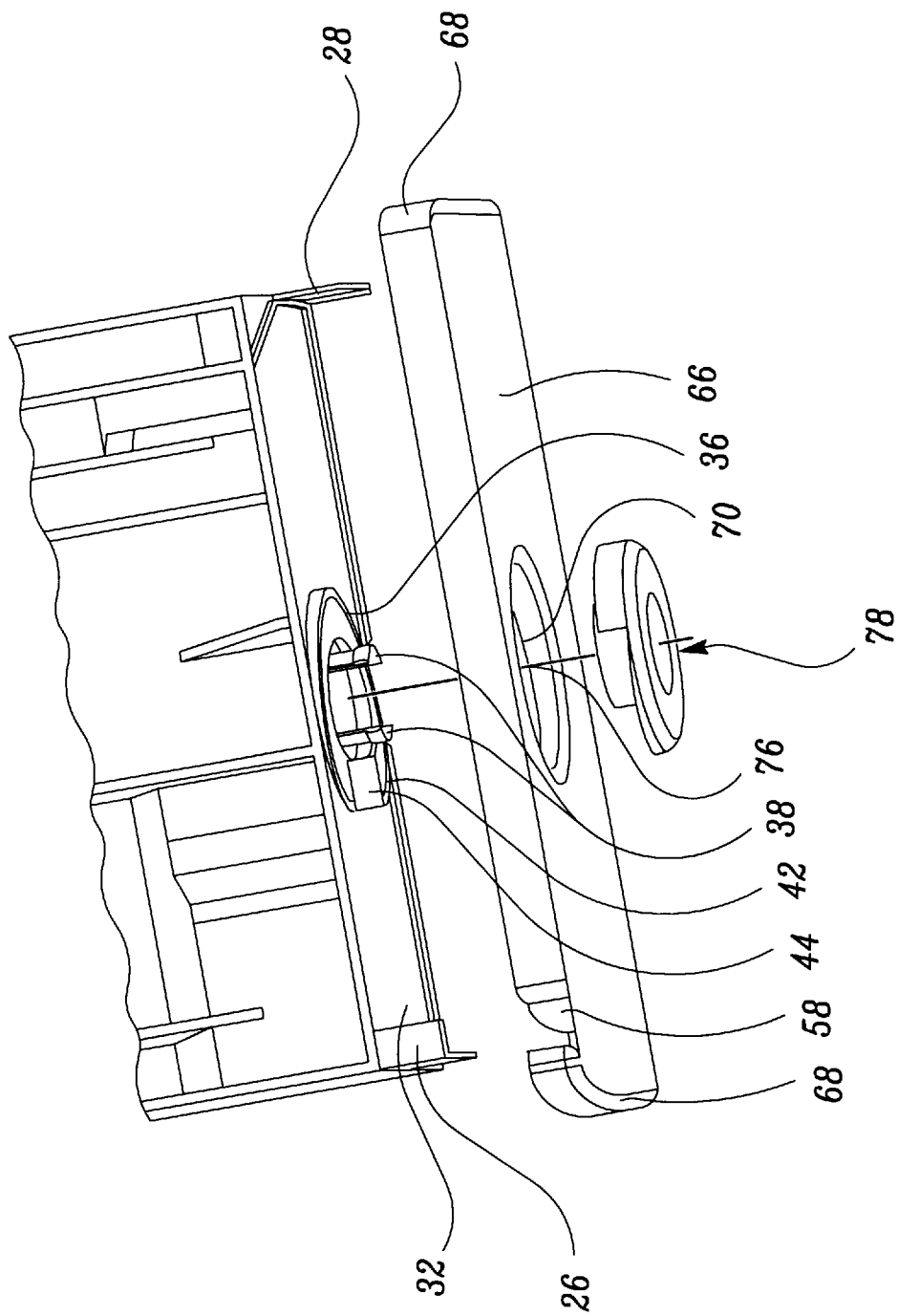
FIG. 5 is a perspective exploded view of the bottom half of the CDU without front face cover and footstand of the present invention.

Referring to FIGS. 2 and 5, a perspective view of the CDU 12 is shown without the face plate 22 in place. Depending feet 26 and 28 are shown extending from the CDU bottom 32. In a central area 34 of CDU bottom 32 a generally helical or spiral ramp 36 is provided surrounding a pair of connection tabs 38 (see FIG. 5). The ramp 36 depends from the surface of the CDU bottom 32 having a first portion 40 being flush with the CDU bottom 32 and ending at a second portion 42 depending the greatest distance from the surface of the CDU bottom 32. A shoulder 44 extends between the first and second portions 40 and 42. However, the particular direction (i.e. clockwise or counterclockwise) the ramp depends from the CDU bottom is not important. It is only necessary that the ramp interact with the other parts of the CDU footstand to provide a variable height stand as discussed further below.

Figure 3:
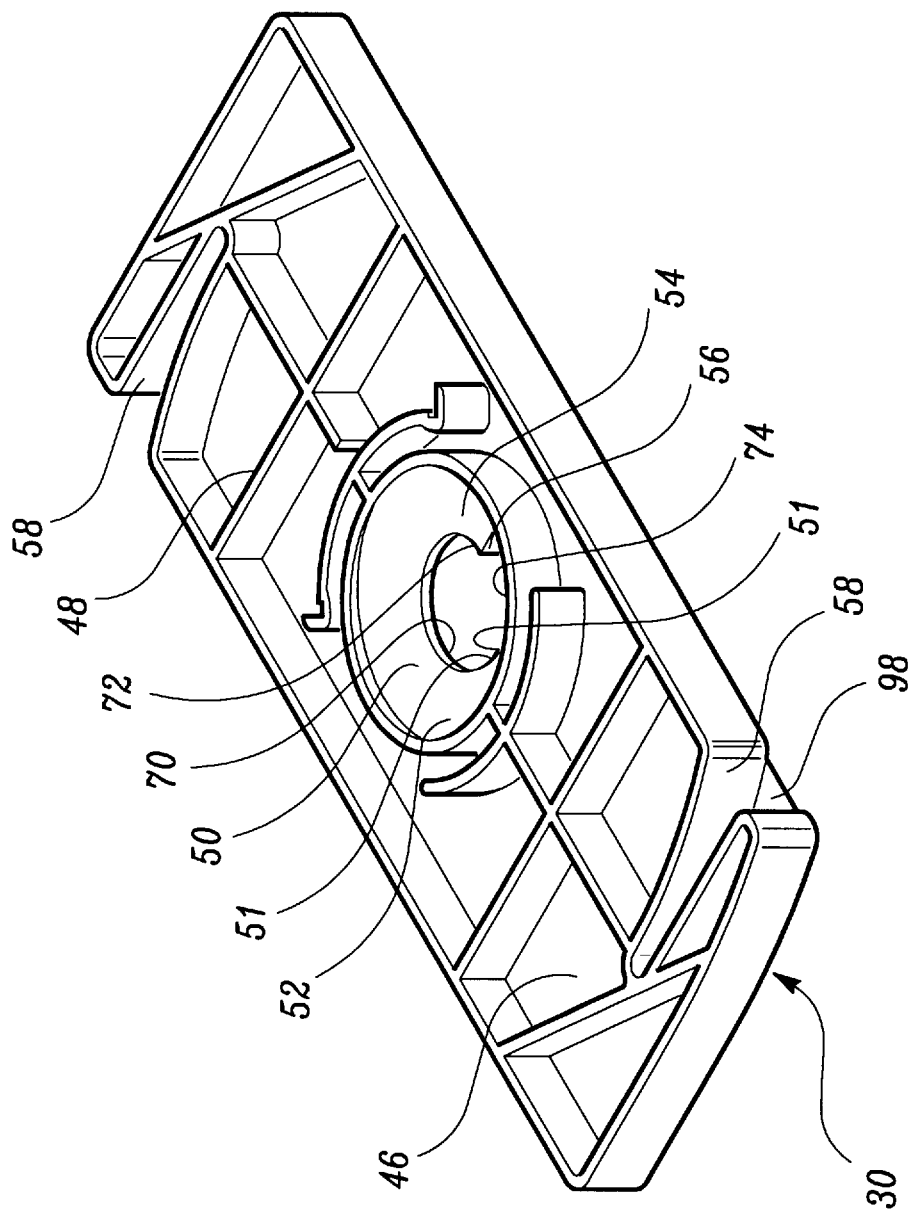
FIG. 3 is a perspective view of the footstand of the present invention.
Figure 8:
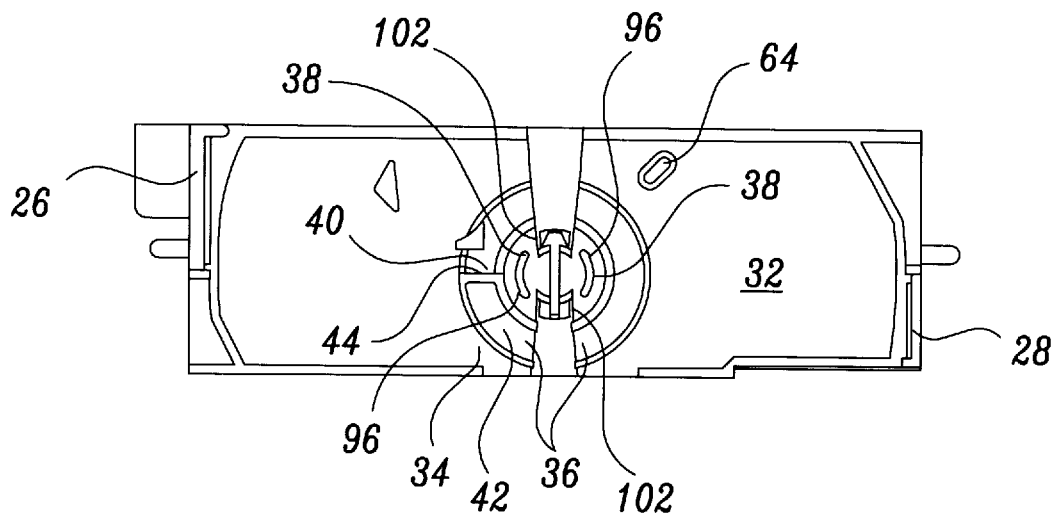
FIG. 8 is a bottom view of the CDU body of the present invention.
Figure 9:
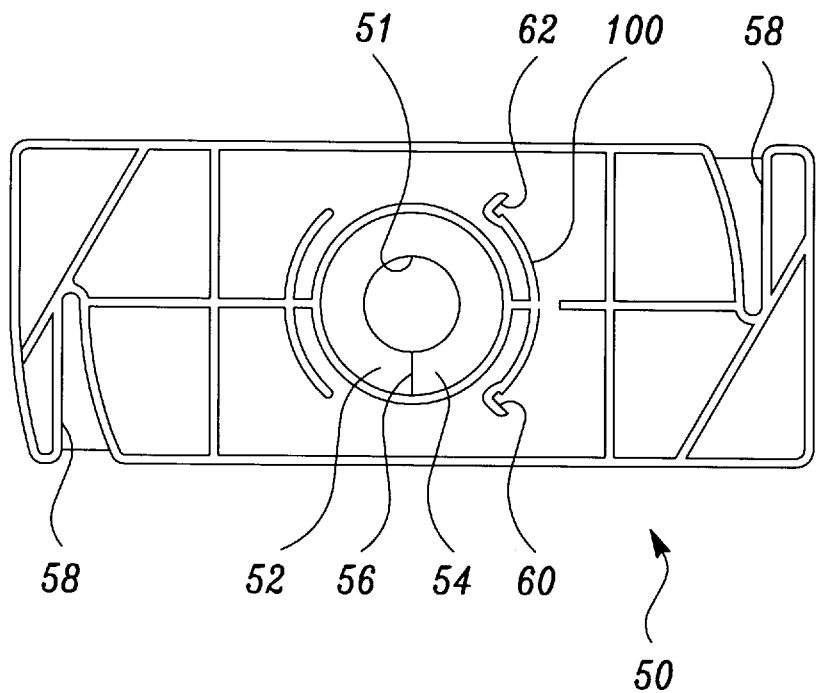
FIG. 9 is an enlarged top view of the footstand of the present invention.
Figure 10:
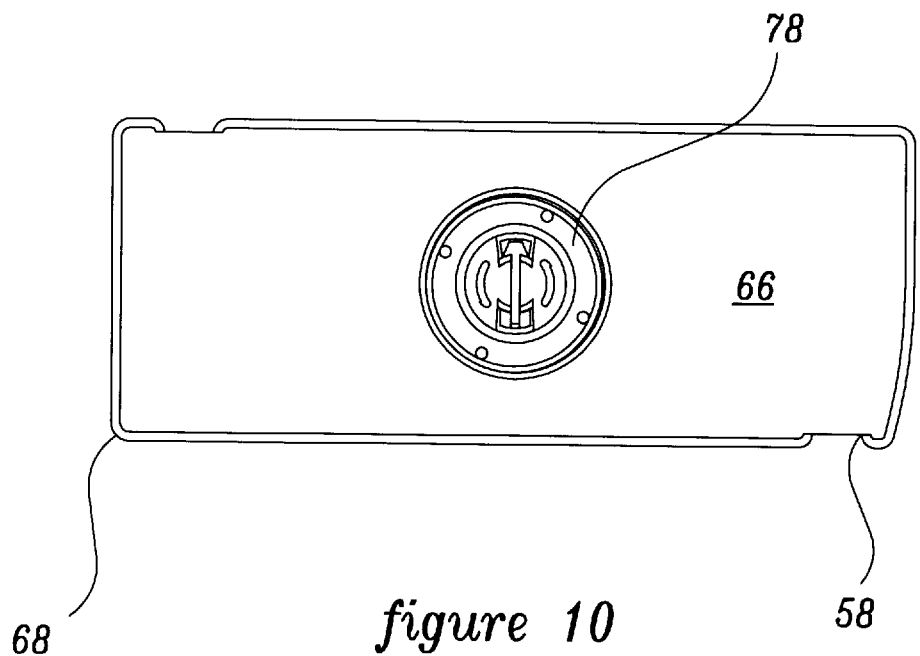
FIG. 10 is an enlarged bottom view of the CDU and footstand of the present invention, showing the footstand in its first, undeployed position protecting the bottom of the CDU body.
Figure 11:
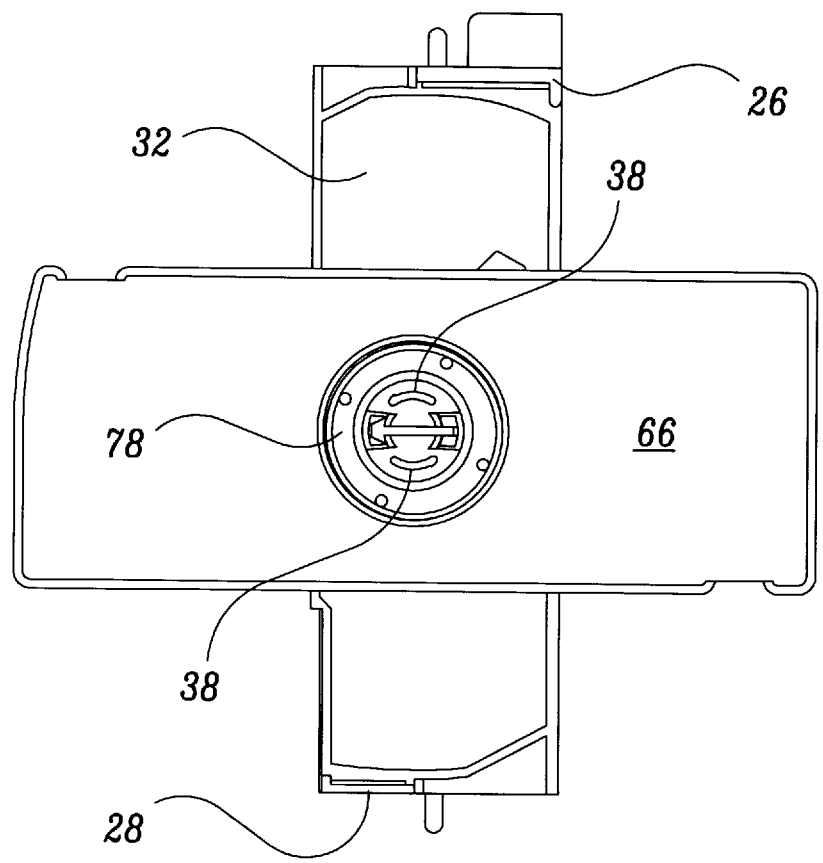
FIG. 11 is an enlarged bottom view of the CDU footstand of the present invention, showing the footstand in its second, deployed position stabilizing and supporting the CDU body against upset.

Referring now to FIG. 3, a perspective view of the footstand 30 is shown. The upper surface 46 of stand 30 is shown having a plurality of ribs 48 to provide the footstand with appropriate strength to support the CDU 10. The stand 30 is provided with a helical or spiral ramp having a matching shape to the depending ramp 36 of the CDU body 12 and having a circular opening 51 therethrough. The ramp 50 is provided with a depressed first portion 52 and a heightened second portion 54 which created a shoulder 56 between the first and second portion 52 and 54. The upper surface 46 of stand 30 is also provided with cutouts 58 which receive the depending feet 26 and 28 as more fully discussed below. The stand is also provided with a pair of detents 60 and 62 which interact with a special rib 64 provided on the CDU bottom 32 as shown in FIGS. 8 and 9. The operation of said rib 64 and detents 60 and 62 will be more fully discussed below. The stand 30 is provided with a completely smooth bottom 66 as shown in FIG. 10. The footstand bottom 66 is also provided with smooth rounded corners 68 so as to provide a CDU having no sharp projections extending from the bottom of the CDU. The helical or spiral ramp 50 has a matching bottom surface 70 having a first portion 72 and second portion 74 defining a shoulder 76 on the opposite side of shoulder 56.

Figure 4:
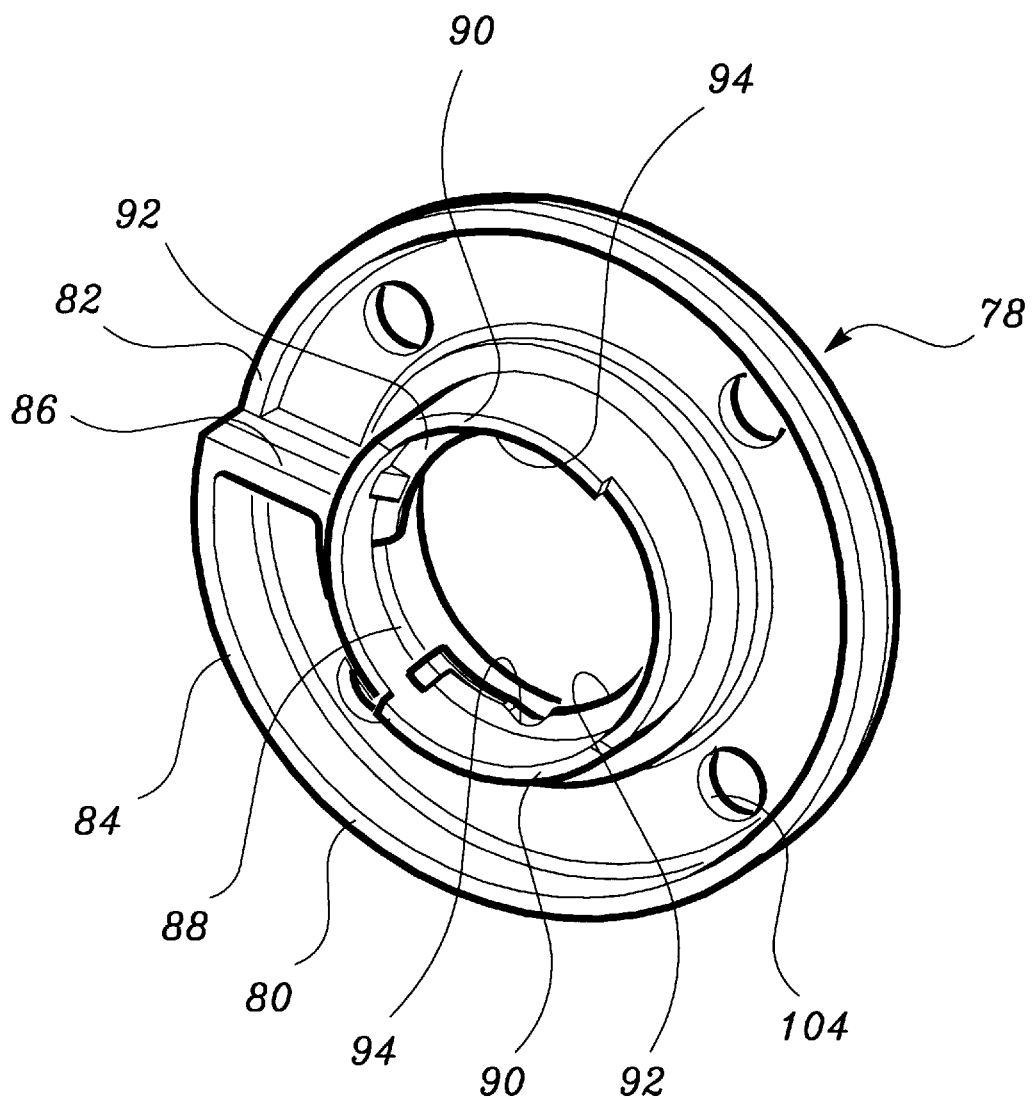
FIG. 4 is an enlarged perspective view of the footstand retainer for use with the present invention.

Referring now to FIG. 4, an enlarged perspective view of a footstand retainer 78 is shown. The retainer 78 also has a ramping surface 80 including a first depressed portion 82 and curving around 360° in a clockwise direction to a second heightened portion 84. A shoulder 86 is provided between first and second portions 82 and 84. Again the ramping surface 80 of retainer 78 generally matches the ramps of both the stand 30 and CDU bottom 32. The retainer 78 further includes generally circular inner collar 88 having a pair of upwardly extending tongs 90. The inner collar 88 has a pair of radially inwardly extending ribs 92 each having a generally semi-circular cutout 94 provided therein. The purpose of the inner collar 88 and inwardly extending ribs 92 will be discussed more fully in relation to FIG. 5 below.

Referring now to FIG. 5, a perspective exploded view of the bottom half of the CDU body 12 is shown in conjunction with stand 30 and retainer 78. The stand 30 is abutted up against the CDU bottom 32 such that the depending connection tabs 38 are received through the circular opening in stand 30. Referring to FIG. 8, the connecting tabs 38 as seen to have a pair of radial projections 96, one projection on each tab. The retainer 78 is placed about connecting tabs 38 such that the radial projections 96 are received within the semi-circular cutouts 94 provided within the inwardly extending ribs 92 of the collar 88. The retainer is twisted in a clockwise direction to snap the retainer 78 in place to affix the retainer 78 to the CDU body 12. However, in this position the stand 30 is free to rotate about 90° about the collar 88 of the footstand retainer 78.

The above description of attaching the footstand retainer to the CDU body is but one manner of affixing the retainer to the body while allowing the stand to rotate about the CDU body and retainer. However, there are many ways to accomplish the above connection such as a snap fit, threaded connection, solvent welding or ultrasonic welding. Any of these methods would suffice as long as the stand is allowed to rotate about the retainer and CDU.

In operation, the rotation of the stand 30 about the CDU body 12 and retainer 78 is discussed more fully in conjunction with FIGS. 6–10 and as discussed below. The various ramps 36, 50 and 70 and ramping surface 80 are configured such that when the stand 30 is in its first, undeployed position as shown in FIG. 6 so that the feet 26 and 28 are enclosed within the stand cutouts 58 and the bottom of stand 30 is a distance "H1" away from the CDU bottom 32. The stand 30 also extends laterally beyond the borders of the CDU body as can be seen in FIGS. 6 and 10 so that no sharp edges extend below the CDU body. In the closed or undeployed position, the stand 30 acts as a packing base, covers and protects the depending feet or legs during shipment, storage and disposal.

Referring now to FIGS. 1 and 7, the CDU and stand 30 are shown with the stand in a second deployed position such that the stand has been rotated in a counter clockwise direction (in reference to FIG. 10) approximately 90° to support the CDU in secure upright position. Referring particularly to FIG. 7, upon rotation of stand 30 to the position shown therein, the ramp 70 of the stand 30 interacts with the ramping surface 80 of the retainer 78 to pull the stand 30 closer to the CDU bottom 32 by a distance of approximately 0.054 inches. The bottom of stand 30 is now a distance "H2" from the CDU bottom 32. The distance of 0.054 inches is not particularly critical, that distance simply being the thickness 98 of the bottom of the stand in the webbed area plus an appropriate clearance between the top of web and foot 26 or 28 which covers the depending feet 26 and 28 of the CDU bottom 32. If the stand thickness 98 was larger or smaller, the distance of travel and change of height between the stand 30 and CDU bottom 32 during 90° rotation of the stand 30 would be changed accordingly by varying the ramps of the respective parts of the retainer, stand and CDU bottom. It is critical that the bottom of the stand 30 be in the same general horizontal plane as the bottom of the depending feet 26 and 28 of the CDU. In this fashion a secure, stable footstand is provided for a medical device such as a CDU.

Referring now to FIGS. 8 and 9, an enlarged bottom view of the CDU bottom 32 and an enlarged top view of the stand 30 are shown. When the stand 30 and CDU bottom are aligned in the first undeployed position as shown in FIG. 6, the rib 64 rests in the detent 60 to bias the stand 30 to stay in the closed or undeployed position. However, upon counter clockwise rotation (as seen in FIG. 10) of the stand 30 relative to the CDU 10 the rib 64 travels along generally arcuate surface 100 until the stand 30 has been rotated approximately 90° and rib 64 now rests in detent 62 to hold or bias the stand 30 to stay in its second deployed position supporting the CDU against upset.

With proper orientation of the various ramps 36, 50, 70, and 80 and their respective shoulders 44, 56, 76, and 86, physical stops are provided which indicate the end of rotation of the stand 30 relative to the CDU bottom 32. When the stand 30 is being moved from the first undeployed position to the second deployed position, shoulder 56 will abut against shoulder 44 of the CDU bottom to prevent the stand 30 from rotating beyond 90° and its appropriate supporting position as shown in FIG. 1. Upon rotation of the stand 30 from the second deployed position to the first undeployed position shown in FIG. 6, the shoulder 76 will contact shoulder 86 of the retainer 78 to prevent the stand from rotating past its first undeployed position shown in FIG. 6.

Referring now to FIG. 10, the bottom of the CDU and stand 30 are shown in the first undeployed position. As can be appreciated the stand bottom 66 is provided with a smooth surface and has rounded corners 68. The retainer 78 is shown affixed in place to the CDU bottom 32. In this view, the connection tabs 38 of the CDU bottom 32 can be seen extending through the retainer collar 88. The CDU bottom 32 is also provided with stops 102 which prevent over rotation of the retainer 78 when securing the stand 30 and retainer 78 to the bottom of the CDU. One end of each of the inwardly extending ribs 92 of the retainer 78 contact the stops 102 to prevent further rotation of the retainer 78 relative to the CDU bottom 32. To assist in rotating the retainer relative to the CDU bottom 32, four holes 104 are provided in the bottom of the retainer 78 for receiving a twisting tool (not shown).

While in accordance with provisions of the statutes there is described herein preferred embodiments of the invention, those skilled in the art will appreciate that changes may be made in the form of the invention covered by the claims appended hereto without departing from the scope and spirit thereof, and that certain features of the invention may sometimes be used to an advantage without corresponding use of the other features. For example, the particular manner of connection of the footstand retainer to the bottom of the CDU is not critical. It is more important that a footstand be provided that covers and protects the bottom of the CDU is its undeployed position and can be rotated to a second position where the bottom of the footstand is flush or on the same horizontal plane as the bottom of the depending feet of the CDU body to provide a stable and secure footstand for the CDU or other like medical device.

We claim:

1. A footstand in combination with a medical container having a generally rectangular configuration, comprising:

at least one depending foot extending from the bottom of said container;

a rotatable stand having at least one cutout which receives the at least one depending foot of the container when said stand is in a first undeployed position wherein said stand is in substantial alignment with the bottom of the container, the stand having a smooth and continuous bottom surface covering the bottom of said depending foot of the container when said stand is in the first undeployed position, the rotatable stand being movable to a second deployed position wherein said stand extends outwardly from two sides of the container to stabilize the container, the stand moving closer to the container during rotation of the stand from the first undeployed position to the second deployed position so that said bottom surface lies in the same horizontal plane as the bottom of the at least one depending foot of the container.

2. The combination according to claim 1, wherein the container is a chest drainage unit (CDU) for receiving and collecting fluids from a patient.

3. The combination according to claim 2, wherein the CDU has two depending feet, one foot on each side of the bottom of the CDU.

4. The combination according to claim 3, wherein the stand has two cutouts for receiving the two depending feet from the bottom of the CDU when said stand is in the first undeployed position.

5. The combination according to claim 2, further comprising:

the CDU including a body having a pair of depending feet, one depending foot on each side of the body;

the rotatable stand being rotatably connected to a central location of a bottom of the body, and having a spiral ramp positioned about the axis of said connection to said CDU body, the ramp adapted to change the distance of the stand from the bottom of the CDU body during rotation of the stand from the first, undeployed position to the second deployed position.

6. The combination according to claim 5, further comprising:

the stand having an upper spiral ramp and a lower spiral ramp, both ramps being coaxial about the connection between the stand and CDU body; and a footstand retainer adapted for connection to the bottom of the body sandwiching the rotatable stand between the retainer and body, the retainer having an upper spiral ramp adapted to cooperatively mate with the lower spiral ramp on the stand to change the distance of the stand from the CDU bottom during rotation of the stand between the first, undeployed position to the second, deployed position.

7. The combination according to claim 6, wherein the upper spiral ramp of the stand has a shoulder adapted to contact a stop on the bottom of the CDU body to prevent the stand from being rotated past the second, deployed position and the lower spiral ramp of the stand has a shoulder adapted to contact a stop on the retainer to prevent the stand from being rotated past the first, undeployed position.

8. The combination according to claim 5, further comprising:

the CDU bottom having a depending rib; and the stand having a pair of detents, one detent receiving said depending rib when the stand is in the first, undeployed position and the other detent receiving said depending rib when the stand is in the second, deployed position, the detents acting to provide a physical indication that said stand has reached either the first and second positions and to temporarily hold said stand in such a position until physical rotation back to its original position by a user.

9. The combination footstand according to claim 1, wherein the stand moves toward the container approximately 0.054 inches during rotation of said stand between the first undeployed position to the second deployed position.

10. A footstand in combination with a medical container having a generally rectangular body, comprising:

a depending foot extending from the bottom of the body;

a rotatable stand having a cutout for receiving the depending foot of said body when said stand is in a first undeployed position such that said stand is in substantial alignment with the bottom of said body, the stand having a smooth and continuous bottom surface covering the bottom of said depending foot when said stand is in the first undeployed position, the stand being rotatable to a second deployed position wherein said stand extends outwardly from two sides of the body to stabilize the container; and height adjust means for changing the distance the stand is from the body such that when the stand is in the first undeployed position the stand covers and protects the depending foot of the body, and when the stand is rotated to the second deployed position the bottom surface of the stand lies in the same horizontal plane as the bottom of the depending foot of the body to provide a secure and stable footstand for such medical container.

11. The combination according to claim 10, wherein the container is a chest drainage unit (CDU) for receiving and collecting fluids from a patient.

12. The combination according to claim 11, further comprising two depending feet from said body, one foot on each side of the body.

13. The combination according to claim 12, wherein the stand has two cutouts for receiving the two depending feet when said stand is in the first undeployed position.

14. The combination according to claim 11, the height adjustment means comprises:

the bottom of said body having a depending spiral ramp about a vertical axis;

the rotatable stand being rotatably connected to the bottom of said body at the vertical axis of the spiral ramp of said body, the stand having an upper spiral ramp cooperatively adapted to mate with the spiral ramp of said body and a lower spiral ramp having the same vertical axis of said upper spiral ramp; and a footstand retainer adapted for connection to the bottom of said body for holding said stand to the CDU body, the retainer having an upper spiral ramp adapted to cooperatively mate with the lower spiral ramp of the stand, such that when the stand is in the first undeployed position the stand covers and protects the depending foot of the body, and when the stand is rotated to the second deployed position the bottom surface of the stand lies in the same horizontal plane as the bottom of the depending foot of the body.

15. The combination according to claim 14, wherein the upper spiral ramp of the stand has a shoulder adapted to contact a shoulder on the bottom spiral ramp of the CDU body to prevent the stand from being rotated past the second deployed position and the lower spiral ramp of the stand has a shoulder adapted to contact a shoulder on the upper spiral ramp of the retainer to prevent the stand from being rotated past the first undeployed position.

16. The combination according to claim 11, wherein the outer perimeter of the stand is larger than the outer perimeter of the CDU body.

17. The combination according to claim 16, wherein the stand is provided with smooth and rounded corners such that when said stand is in the first undeployed position protecting the bottom of said CDU no sharp corners or protrusions extend outwardly from the bottom of said CDU.

18. The combination according to claim 10, further comprising:

the CDU bottom having a depending rib; and the stand having a pair of detents, one detent receiving said depending rib when the stand is in the first undeployed position and the other detent receiving said depending rib when the stand is in the second deployed position, the detents temporarily holding the stand in either of the first or second position.

19. The combination according to claim 10, wherein the stand moves toward the body approximately 0.054 inches during rotation of said stand between the first undeployed position and the second deployed position.

* * * * *